(12) United States Patent
Zablocki et al.

(10) Patent No.: US 7,601,721 B2
(45) Date of Patent: Oct. 13, 2009

(54) SUBSTITUTED HETEROCYCLIC COMPOUNDS

(75) Inventors: Jeff Zablocki, Mountain View, CA (US); Dmitry Koltun, Foster City, CA (US)

(73) Assignee: Gilead Palo Alto, Inc., Palo Alto, CA (US)

( * ) Notice: Subject to any disclaimer, the term of this patent is extended or adjusted under 35 U.S.C. 154(b) by 0 days.

(21) Appl. No.: 11/856,712

(22) Filed: Sep. 17, 2007

(65) Prior Publication Data

US 2008/0070927 A1    Mar. 20, 2008

Related U.S. Application Data

(63) Continuation of application No. 11/222,452, filed on Sep. 7, 2005, now Pat. No. 7,271,169.

(60) Provisional application No. 60/608,384, filed on Sep. 8, 2004.

(51) Int. Cl.
*A61K 31/496*    (2006.01)
*C07D 277/64*    (2006.01)
*C07D 263/56*    (2006.01)
*C07D 417/12*    (2006.01)

(52) U.S. Cl. .................. 514/254.03; 544/368; 544/364; 514/253.1

(58) Field of Classification Search .................. 544/368; 514/254.03

See application file for complete search history.

(56) References Cited

FOREIGN PATENT DOCUMENTS

DE    2824764    * 12/1979

* cited by examiner

*Primary Examiner*—Emily Bernhardt
(74) *Attorney, Agent, or Firm*—J. Elin Hartrum; Daniel W. Collins

(57) ABSTRACT

Disclosed are novel piperazine and piperazine derivatives, useful for the treatment of various disease states, in particular cardiovascular diseases such as atrial and ventricular arrhythmias, diabetes, intermittent claudication, Prinzmetal's (variant) angina, stable and unstable angina, exercise induced angina, congestive heart disease, and myocardial infarction.

17 Claims, No Drawings

SUBSTITUTED HETEROCYCLIC COMPOUNDS

CROSS REFERENCE TO RELATED APPLICATIONS

This application is a Continuation application of U.S. patent application Ser. No. 11/222,452, filed Sep. 7, 2005 (U.S. Pat. No. 7,271,169), which claimed priority to U.S. Provisional Patent Application Ser. No. 60/608,384, filed Sep. 8, 2004, both of which applications are incorporated by reference herein in their entireties.

FIELD OF THE INVENTION

The present invention relates to novel heterocyclic compounds, in particular piperidine and piperazine derivatives, and to their use in the treatment of various disease states, including cardiovascular diseases such as atrial and ventricular arrhythmias, intermittent claudication, Prinzmetal's (variant) angina, stable and unstable angina, exercise induced angina, congestive heart disease, ischemia, reperfusion injury and myocardial infarction, and diabetes and disease states related to diabetes. The invention also relates to methods for their preparation, and to pharmaceutical compositions containing such compounds.

SUMMARY OF THE INVENTION

Certain classes of piperazine compounds are known to be useful for the treatment of cardiovascular diseases, including arrhythmias, angina, myocardial infarction, and related diseases such as intermittent claudication. For example, U.S. Pat. No. 4,567,264 discloses a class of substituted piperazine compounds that includes a compound known as ranolazine, (±)-N-(2,6-dimethylphenyl)-4-[2-hydroxy-3-(2-methoxyphenoxy)-propyl]-1-piperazineacetamide, and its pharmaceutically acceptable salts. Other U.S. patents and U.S. patent applications also disclose piperazine derivatives similarly useful for the treatment of cardiovascular diseases, for example U.S. Pat. Nos. 6,451,798, 6,573,264, and U.S. patent application Ser. Nos. 09/791,134, 09/791,133, 09/791,262, 09/791,134, 10/198,237, 10/729,499, 10/745,224, 10/759,555, and 10/862,798, the complete disclosures of which are hereby incorporated by reference.

Despite the desirable properties demonstrated by ranolazine and similar compounds, which are very effective cardiac therapeutic agents, believed to function, at least in part, as fatty acid oxidation inhibitors, there remains a need for compounds that have similar therapeutic properties to ranolazine, but are more potent and have a longer half-life. One feature common to all of the above classes of therapeutic agents is a hydroxy group on the aliphatic chain, normally at the 2-position. It has now surprisingly been discovered that the hydroxy group can be replaced by certain groups and retain the desired activity as effective cardiac therapeutic agents.

SUMMARY OF THE INVENTION

It is an object of this invention to provide novel substituted piperazine and piperidine derivatives that function as effective cardiac therapeutic agents. Accordingly, in a first aspect, the invention relates to compounds of Formula I:

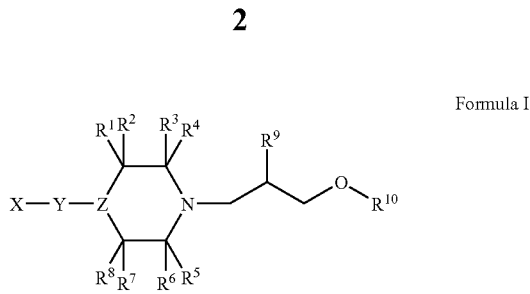

Formula I wherein:
$R^1$, $R^2$, $R^3$, $R^4$, $R^5$, $R^6$, $R^7$, and $R^8$ are hydrogen, lower alkyl, or —C(O)R; in which R is —OR$^9$ or —NR$^{12}$R$^{13}$, where $R^{12}$ and $R^{13}$ are hydrogen or lower alkyl; or
$R^1$ and $R^2$, $R^3$ and $R^4$, $R^5$ and $R^6$, $R^7$ and $R^8$, when taken together with the carbon to which they are attached, represent carbonyl; or
$R^1$ and $R^5$, or $R^1$ and $R^7$, or $R^3$ and $R^5$, or $R^3$ and $R^7$, when taken together form a bridging group —(CR$^{14}$R$^{15}$)$_n$—, in which n is 1, 2 or 3, and $R^{14}$ and $R^{15}$ are independently hydrogen or lower alkyl;
with the proviso that
(i) the maximum number of carbonyl groups is 2; and
(ii) the maximum number of bridging groups is 1;
$R^9$ is —NHSO$_2$R$^{12}$, —NHC(O)R$^{12}$, or —OR$^{12}$;
in which $R^{12}$ is optionally substituted lower alkyl; and
$R^{10}$ is optionally substituted aryl or optionally substituted heteroaryl;
X is optionally substituted aryl, optionally substituted heteroaryl, or optionally substituted dihydroheteroaryl;
Y is (CH$_2$)$_n$, in which n is 0, 1, or 2;
Z is —N<, —NH—CH<, —NH—C(O)—N<, or —NH—C(O)—CH$_2$—N<;

and the pharmaceutically acceptable salts, esters, polymorphs, and prodrugs thereof.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that is amenable to treatment by a fatty acid oxidation inhibitor. Such diseases include, but are not limited to, protection of skeletal muscles against damage resulting from trauma, intermittent claudication, shock, and cardiovascular diseases including atrial and ventricular arrhythmias, Prinzmetal's (variant) angina, stable angina, exercise induced angina, congestive heart disease, diabetes, and myocardial infarction. The compounds of Formula I are also useful for lowering plasma level of HbA1c, lowering glucose plasma levels, lowering total cholesterol plasma levels, lowering triglyceride plasma levels, raising HDL cholesterol levels, and/or delaying onset of diabetic retinopathy. They can also be used to preserve donor tissue and organs used in transplants.

A fourth aspect of this invention relates to methods of preparing the compounds of Formula I.

The preferred compounds presently include, but are not limited to:
N-fluoren-2-yl(4-{3-(2-methylbenzothiazol-5-yloxy)-2-[(methylsulfonyl)amino]propyl}-piperazinyl)carboxamide;
2-(4-{3-(2-methylbenzothiazol-5-yloxy)-2-[(methylsulfonyl)amino]propyl}piperazinyl)-N-(3-phenylphenyl)acetamide;

N-{2-[4-(N-fluoren-2-ylcarbamoyl)piperazinyl]-1-[(2-methylbenzothiazol-5-yloxy)methyl]ethyl}acetamide;

2-{4-[2-(acetylamino)-3-(2-methylbenzothiazol-5-yloxy)propyl]piperazinyl}-N-(3-phenylphenyl)acetamide; and 5-{(2R)-2-methoxy-3-[4-({5-[4-(trifluoromethyl)phenyl](1,2,4-oxadiazol-3-yl)}methyl)piperazinyl]propoxy}-2-methylbenzothiazole.

DEFINITIONS AND GENERAL PARAMETERS

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, preferably having from 1 to 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$R$_a$, in which R$_a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Preferred aryls include phenyl, fluorenyl, naphthyl and the like.

Unless otherwise constrained by the definition for the aryl substituent, such aryl groups can optionally be substituted with 1, 2, 3, 4 or 5 substituents, preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" or refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "dihydroheteroaryl" refers to a heteroaryl group as defined above in which one double bond has been saturated, and one double bond remains unsaturated. That is, a partially saturated heteroaryl group. Examples of such groups are:

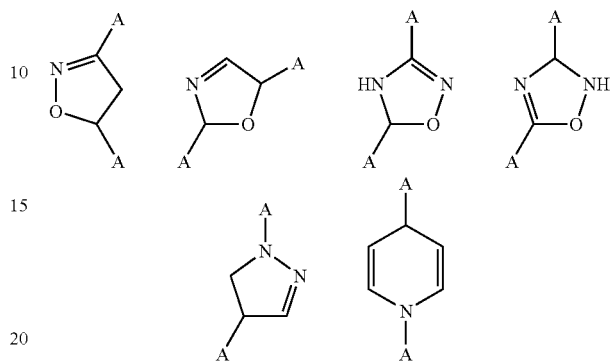

in which A represents the points of attachment, which are derivatives of; 3,5-(4,5-dihydroisoxazole), 2,5-(1,3-oxazoline), 3,5-(2,3-dihydro-1,2,4-oxadiazole), 3,5-(4,5-dihydro-1,2,4-oxadiazole), 1,4-pyrazoline, 4,5-dihydropyridine, and the like.

Unless otherwise constrained by the definition for the dihydroheteroaryl substituent, such dihydroheteroaryl groups can be optionally substituted in the same manner as heteroaryl.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "compound of Formula I" is intended to encompass the compounds of the invention as disclosed, and the pharmaceutically acceptable salts, pharmaceutically acceptable esters, polymorphs, and prodrugs of such compounds.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Fatty acid oxidation inhibitors" refers to compounds that suppress ATP production from the oxidation of fatty acids and consequently stimulate ATP production from the oxidation of glucose and lactate. In the heart, most of the ATP production is acquired through the metabolism of fatty acids. The metabolism of glucose and lactate provides a lesser proportion of ATP. However, the generation of ATP from fatty acids is less efficient with respect to oxygen consumption than the generation of ATP from the oxidation of glucose and lactate. Thus, the use of fatty acid oxidation inhibitors results in more energy production per molecule of oxygen consumed, allowing the heart to be energized more efficiently. Fatty acid oxidation inhibitors are especially useful, therefore, for treating an ischemic environment in which oxygen levels are reduced.

Nomenclature

The naming and numbering of the compounds of the invention is illustrated with a representative compound of Formula I in which where X is 3-phenylphenyl, $R^9$ is —$NHSO_2CH_3$, Z is —NH—C(O)—$CH_2$—, $R^1$, $R^2$, $R^3$, $R^4$, $R^5$, $R^6$, $R^7$, and $R^8$ are hydrogen, and $R^{10}$ is 2-methylbenzothiazol-5-yl:

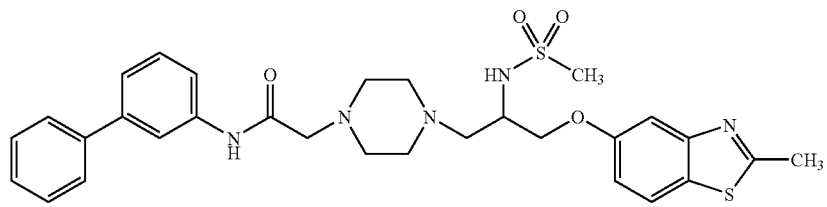

namely:

2-(4-{3-(2-methylbenzothiazol-5-yloxy)-2-[(methylsulfonyl)amino]propyl}piperazinyl)-N-(3-phenylphenyl)acetamide.

Synthesis of the Compounds of Formula I

The compounds of Formula I in which $R^9$ is a nitrogen-substituted moiety and Z is —N< may be prepared from an intermediate of formula (8), the preparation of which is shown in Reaction Scheme I.

REACTION SCHEME 1

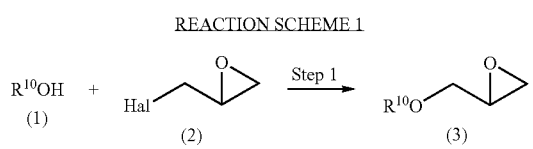

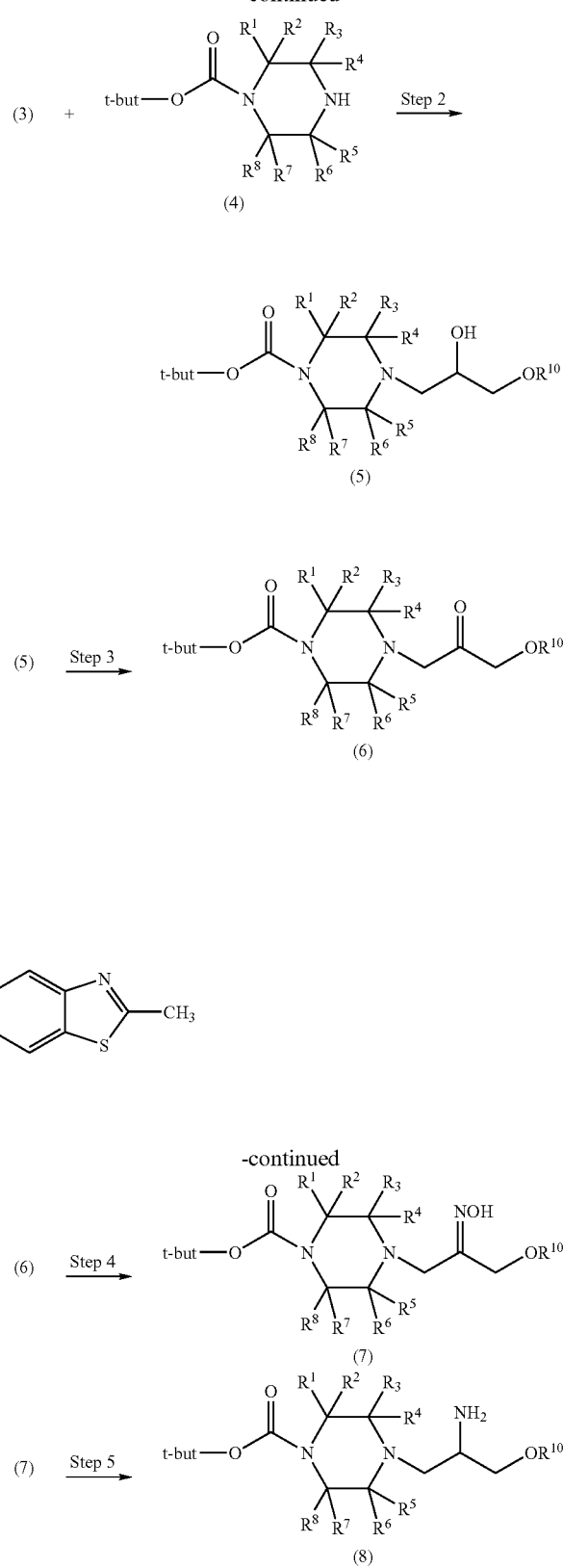

in which $R^1$, $R^2$, $R^3$, $R^4$, $R^5$, $R^6$, $R^7$, $R^8$ and $R^{10}$ are as defined in the Summary of the Invention.

Starting Materials

The compounds of formula (1), (2), and (4) are either commercially available or can be made by conventional methods well known to those of ordinary skill in the art. For example, the precursor to a compound of formula (4) where $R^1$ and $R^5$ when taken together represent a bridging methylene group, i.e.;

is commercially available [(1S,4S)-(+)-2,5-diazabicyclo[2.2.1]heptane], or can be made by a procedure disclosed in J. Org. Chem., 1990, 55, 1684-7. Similarly, the precursor to a compound of formula (4) where $R^1$ and $R^5$ when taken together represent a bridging methylene group, and the precursor to a compound of formula (4) where $R^1$ and $R^7$ when taken together represent a bridging methylene group, can be made by published procedures found in J. Med. Chem., 1974, 17, 481-7. The precursor to a compound of formula (4) in which $R^1$, $R^2$, $R^3$, $R^4$, $R^5$, $R^6$, and $R^7$ are hydrogen and $R^8$ is —C(O)NH$_2$ is prepared from piperazine-2-carboxamide, a commercially available compound.

Step 1—Preparation of Formula (3)

The compound of formula (3) is prepared conventionally by reaction of a compound of formula (1), for example 5-hydroxy-2-methylbenzothiazole, with an epoxide of formula (2), which may be racemic or chiral. In general, the two compounds are mixed in an inert solvent, preferably a ketone, for example acetone, and a tertiary organic base or an inorganic base, preferably potassium carbonate, at a temperature of about reflux, for about 8-48 hours, preferably overnight. When the reaction is substantially complete, the product of formula (3) is isolated by conventional means, for example by filtration, removal of the solvent under reduced pressure, followed by chromatography of the residue on silica gel. Alternatively, after filtration the product can be crystallized from the filtrate.

Step 2—Preparation of Formula (5)

The epoxide of formula (3) is then reacted with a protected piperazine of formula (4), which is commercially available or prepared by means well known in the art. In general, the two compounds are mixed in an inert solvent, preferably a halogenated solvent, for example methylene chloride, optionally in the presence of a catalyst, for example ytterbium (III) trifluoromethanesulfonate. If the reaction is carried out in the presence of a catalyst, the reaction is conducted at about 0-30° C., preferably at about room temperature, for about 8-48 hours, preferably overnight. In the absence of a catalyst, the mixture is refluxed for about 1-24 hours in ethanol. When the reaction is substantially complete, the product of formula (5) is isolated by conventional means, for example by removal of the solvent under reduced pressure, followed by chromatography of the residue on silica gel.

Step 3—Preparation of Formula (6)

The compound of formula (5) is then oxidized to a ketone utilizing the well-known Swern oxidation. In general, dimethylsulfoxide is added to an inert solvent, preferably a halogenated solvent, for example methylene chloride, and cooled to about −80° C. To this mixture is added a solution of oxalyl chloride in an inert solvent, for example methylene chloride, followed by a solution of the compound of formula (5) in an inert solvent, for example methylene chloride. To the reaction mixture is added a tertiary base, for example triethylamine, and the mixture stirred for a few minutes. The mixture is then allowed to warm to about room temperature. When the reaction is substantially complete, the product of formula (6) is isolated by conventional means, for example by extraction with a solvent, for example ethyl acetate, and removal of the dried solvent layer under reduced pressure. The residue can be purified, for example by chromatography on silica gel, or can be used in the next reaction with no further purification.

Step 4—Preparation of Formula (7)

The compound of formula (6) is then converted to a hydroxylamine derivative of formula (7). In general, the ketone of formula (6) is added to an inert solvent, for example tetrahydrofuran, at about room temperature. To this solution is added hydroxylamine hydrochloride and an excess of a tertiary base, for example triethylamine, and the mixture stirred for 6-24 hours, preferably overnight. The mixture is then allowed to warm to about room temperature. When the reaction is substantially complete, the product of formula (7) is isolated by conventional means, for example by extraction with a solvent, for example methylene chloride, and removal of the dried solvent layer under reduced pressure. The residue can be purified, for example by chromatography on silica gel, or can be used in the next reaction with no further purification.

Step 5—Preparation of Formula (8)

The compound of formula (7) is then reduced to an amine of formula (8). In general, the hydroxylamine of formula (7) is suspended in a mixture of a protic solvent, for example methanol, a hydrogenation catalyst, for example Raney nickel, and a catalytic amount of a strong acid, for example aqueous hydrobromic acid. The mixture is hydrogenated under pressure for 6-24 hours, preferably overnight, at about room temperature. When the reaction is substantially complete, the product of formula (8) is isolated by conventional means, for example by filtration, adjusting the pH of the filtrate with a strong base, extracting with a solvent, for example methylene chloride, and removal of the dried solvent layer under reduced pressure. The residue can be purified, for example by chromatography on silica gel, or can be used in the next reaction with no further purification.

The compound of formula (8) is then reacted with the appropriate functionalizing agent (for example an anhydride, an acyl halide, or a sulfonyl halide) to provide a compound of formula (9), which is deprotected and then reacted with a compound of formula X—Y-Hal to provide a compound of Formula I in which $R^9$ is —NHSO$_2$R$^{12}$ or —NHC(O)R$^{12}$, as shown in Reaction Scheme II.

REACTION SCHEME II

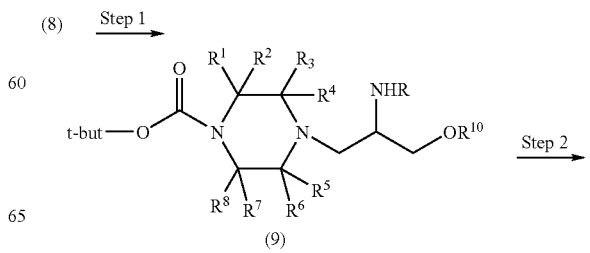

-continued

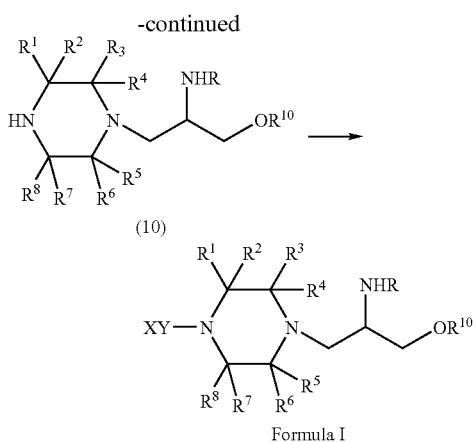

(10)

Formula I where R is —SO$_2$R$^{12}$ or —C(O)R$^{12}$.

Step 1—Preparation of Formula (9) where R is —C(O)R$^{12}$

The compound of formula (9) is prepared conventionally by reaction of a compound of formula (8) with an acyl anhydride of formula (R$^{12}$CO)$_2$O, or an acyl halide of formula R$^{12}$C(O)Hal, where Hal is chloro, bromo or iodo and R$^{12}$ is as defined in the Summary of the Invention. In general, the two compounds are mixed in an inert solvent, for example methylene chloride, in the presence of a tertiary organic base, for example triethylamine, at about 0° C. The temperature is allowed to warm to about room temperature, and left for about 8-48 hours, preferably overnight. When the reaction is substantially complete, the product of formula (9) is isolated by conventional means, for example by partitioning the residue between a solvent and water, removal of the organic solvent under reduced pressure, followed by chromatography of the residue on silica gel.

Step 1—Preparation of a Compound of Formula (9) in which R is —SO$_2$R$^{12}$

To prepare a compound of formula (9) in which R is —SO$_2$R$^{12}$, the compound of formula (8) is reacted with a compound of the formula R$^{12}$SO$_2$Hal, where Hal is chloro, bromo or iodo and R$^{12}$ is as defined in the Summary of the Invention.

In general, the amine of formula (8) is dissolved in an inert solvent, for example methylene chloride at about 0°. To this solution is added a compound of the formula R$^{12}$SO$_2$Hal, and an excess of a tertiary base, for example triethylamine. Reaction is continued for about 6-24 hours, preferably overnight, allowing the temperature to rise to room temperature. When the reaction is substantially complete, the product of Formula I is isolated by conventional means, for example by extraction with a solvent, for example methylene chloride, and removal of the dried solvent layer under reduced pressure. The residue is purified, for example by chromatography on silica gel, to provide a compound of formula (9) in which R is —SO$_2$R$^{12}$.

Step 2—Preparation of Formula (10) where R is —C(O)R$^{12}$ or —SO$_2$R$^{12}$

To prepare a compound of formula (10) in which R is —C(O)R$^{12}$ or —SO$_2$R$^{12}$, the compound of formula (9) in which R is —C(O)R$^{12}$ or —SO$_2$R$^{12}$ is deprotected by hydrolysis of the t-butyl ester. In general, the compound of formula (9) is dissolved in a mixture of an inert solvent, for example methylene chloride or dioxane, and a strong acid, for example hydrochloric acid or trifluoroacetic acid. The reaction is conducted at about 0-30° C., preferably at about room temperature, for about 8-48 hours, preferably overnight. When the reaction is substantially complete, the product of formula (10) is isolated by conventional means, for example by adding a base to remove excess acid, and removal of the solvent under reduced pressure.

Step 4—Preparation of a Compound of Formula I

The compound of formula (10) is then reacted with a compound of formula X—Y-Hal, in which X and Y are as defined in the Summary of the Invention, and Hal is chloro, bromo or iodo. Such compounds are either commercially available, or prepared by means well known in the art. In general, the two compounds are mixed in an inert solvent, preferably a polar solvent, for example N,N-dimethylformamide, in the presence of a tertiary organic base, for example triethylamine. The reaction is conducted at about 30-100° C., preferably at about 50-60° C., for about 1-12 hours, preferably about 4 hours. When the reaction is substantially complete, the product of Formula I is isolated by conventional means, for example by removal of the solvent under reduced pressure, followed by chromatography.

Preparation of a Compound of Formula (10) in which R$^9$ is —OR$^{12}$

To prepare a compound of Formula I in which R$^9$ is —OR$^{12}$, a compound of formula (11) is reacted with an alkyl halide.

REACTION SCHEME III

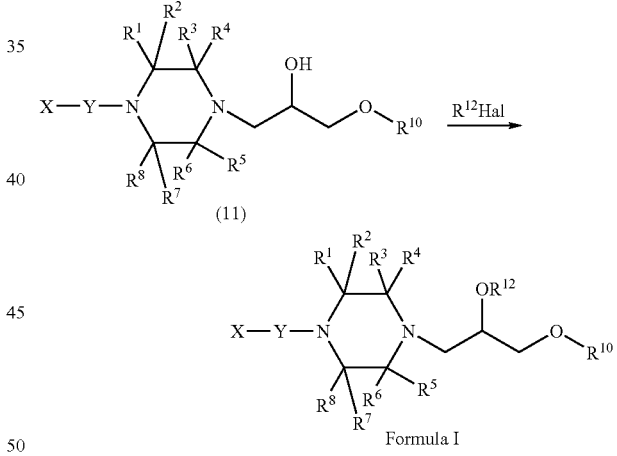

Formula I

To prepare a compound of Formula I in which R$^9$ is OR$^{12}$ and Z is nitrogen, the compound of formula (11) is reacted with a compound of the formula R$^{12}$ Hal, where Hal is chloro, bromo or iodo and R$^{12}$ is as defined in the Summary of the Invention.

In general, the compound of formula (11) in an inert solvent, for example toluene, is added to a suspension of a strong base, for example sodium hydride, in an inert solvent, for example toluene at a temperature of about 0° C. The mixture is then warmed to about 100° C. for about 1-5 hours, and then cooled to about 0° C. A compound of formula R$^{12}$ Hal is then added, and the mixture stirred for about 6-24 hours, preferably overnight, allowing the temperature to rise to room temperature. When the reaction is substantially complete, the product of Formula I is isolated by conventional means, for example by quenching of the reaction with water, extracting with a solvent, for example ethyl acetate, and removal of the dried solvent layer under reduced pressure. The residue is purified, for example by chromatography on silica gel, to provide a compound of Formula I in which $R^9$ is —$OR^{12}$.

The preparation of a compound of formula (11) starts from a compound of formula (5), the preparation of which is shown in Reaction Scheme I. The preparation of (11) is shown in Reaction Scheme IV, using as an example a compound of formula (9) that is a precursor to a compound of Formula I in which Z is —N<.

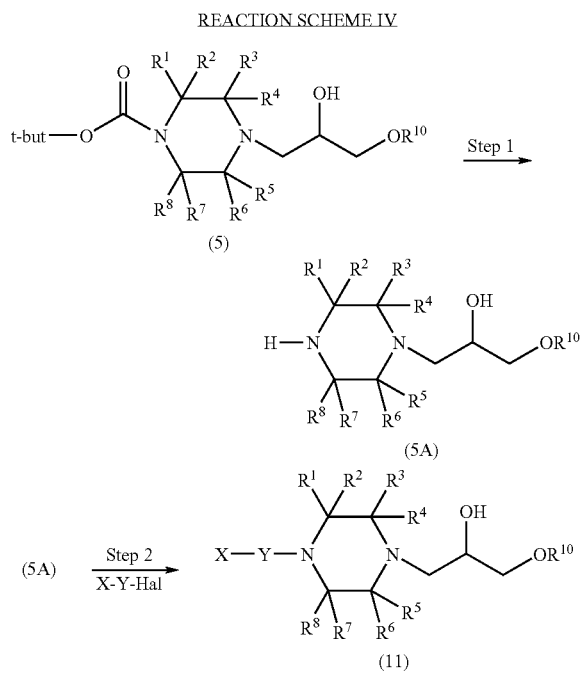

in which $R^1$, $R^2$, $R^3$, $R^4$, $R^5$, $R^6$, $R^7$, $R^8$, $R^{10}$ X and Y are as defined in the Summary of the Invention, Hal is halogen, and t-but is tertiary butyl.

Starting Materials

The compound of formula (5) can be made by conventional methods well known to those of ordinary skill in the art—for example, as described in U.S. patent application Ser. No. 10/198,237, the complete disclosure of which is hereby incorporated by reference.

Step 1—Preparation of Formula (5A)

The compound of formula (5A) is prepared conventionally by deprotection of a compound of formula (5) by hydrolysis of the t-butyl ester. In general, the compound of formula (5) is dissolved in a mixture of an inert solvent, preferably a halogenated solvent, for example methylene chloride, and a strong acid, for example trifluoroacetic acid. The reaction is conducted at about 0-30° C., preferably at about room temperature, for about 8-48 hours, preferably overnight. When the reaction is substantially complete, the product of formula (5A) is isolated by conventional means, for example by adding a base to remove excess acid, and removal of the solvent under reduced pressure.

Step 2—Preparation of a Compound of Formula (11)

The compound of formula (5A) is then reacted with a compound of formula X—Y-Hal, in which X and Y are as defined in the Summary of the Invention, and Hal is chloro, bromo or iodo. Such compounds are either commercially available, prepared by means well known in the art. In general, the two compounds are mixed in an inert solvent, preferably a protic solvent, for example ethanol, in the presence of an inorganic or tertiary organic base, preferably triethylamine. The reaction is conducted at about 30-100° C., preferably at about reflux, for about 8-48 hours, preferably overnight. When the reaction is substantially complete, the product of formula (11) is isolated by conventional means, for example by removal of the solvent under reduced pressure, followed by chromatography.

General Utility

The compounds of Formula I are effective in the treatment of conditions known to respond to administration of fatty acid oxidation inhibitors, including protection of skeletal muscles against damage resulting from trauma, intermittent claudication, shock, and cardiovascular diseases including atrial and ventricular arrhythmias, intermittent claudication, Prinzmetal's (variant) angina, stable angina, unstable angina, ischemia and reperfusion injury in cardiac, kidney, liver and the brain, exercise induced angina, congestive heart disease, myocardial infarction, and diabetes and disease states related to diabetes. The compounds of Formula I can also be used to preserve donor tissue and organs used in transplants, and may be co-administered with thrombolytics, anticoagulants, and other agents.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Compounds of Formula I may be impregnated into a stent by diffusion, for example, or coated onto the stent such as in a gel form, for example, using procedures known to one of skill in the art in light of the present disclosure.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and are generally administered in a pharmaceutically effective amount. Preferably, for oral administration, each dosage unit contains from 1 mg to 2 g of a compound of Formula I, and for parenteral administration, preferably from 0.1 to 700 mg of a compound of Formula I. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (5)

A. Preparation of a Compound of Formula (5) in which $R^1$, $R^2$, $R^3$, $R^4$, $R^5$, $R^6$, $R^7$, and $R^8$ are Hydrogen and $R^{10}$ is 2-Methylbenzothiazol-5-yl

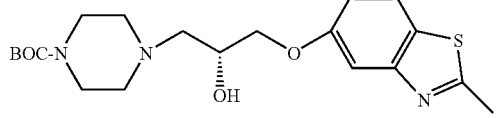

To 2-methyl-5-(oxiran-2-ylmethoxy)benzothiazole (2.21 g, 10 mmol), a compound of formula (3), was added tert-butyl 1-piperazinecarboxylate (1.86 g, 10 mmol), a compound of formula (4), and ethanol (30 ml). The resulting solution was heated to 85° C. and stirred for 8 hours. The solvent was evaporated under reduced pressure, and the residue was chromatographed on silica gel, eluting with 5% methanol/methylene chloride, to yield 4-[2-hydroxy-3-(2-methylbenzothiazol-5-yloxy)propyl]-piperazine-1-carboxylic acid tert-butyl ester as a clear oil (2.9 g, 7.1 mmol).

B. Preparation of a Compound of Formula (5) in which $R^1$, $R^2$, $R^3$, $R^4$, $R^5$, $R^6$, $R^7$ and $R^8$ are Hydrogen, $R^4$ is (S)-Methyl, and $R^{10}$ is 2-Methylbenzothiazol-5-yl

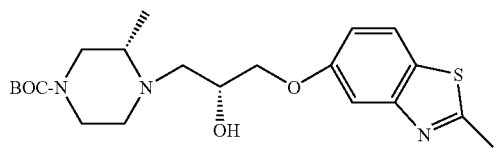

Similarly, following the procedure of Example 1A above, but replacing tert-butyl 1-piperazinecarboxylate with tert-butyl(3S)-3-methylpiperazinecarboxylate, the following compound of formula (5) is prepared.

tert-butyl(3S)-4-[(2R)-2-hydroxy-3-(2-methylbenzothiazol-5-yloxy)propyl]-3-methylpiperazinecarboxylate.

C. Preparation of Compounds of Formula (5), Varying $R^1$, $R^2$, $R^3$, $R^4$, $R^5$, $R^6$, $R^7$, $R^8$, and $R^{10}$ Similarly, following the procedure of Example 1A or IB above, but optionally replacing tert-butyl 1-piperazinecarboxylate with other compounds of formula (4) and optionally replacing 2-methyl-5-(oxiran-2-ylmethoxy)benzothiazole with other compounds of formula (3), other compounds of formula (5) are prepared.

EXAMPLE 2

Preparation of a Compound of Formula (6)

A. Preparation of a Compound of Formula (6) in which $R^1$, $R^2$, $R^3$, $R^4$, $R^5$, $R^6$, $R^7$, and $R^8$ are Hydrogen, and $R^{10}$ is 2-Methylbenzothiazol-5-yl

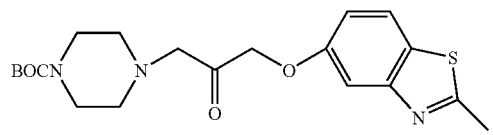

A mixture of dimethylsulfoxide (62 μl, 0.88 mmol) and methylene chloride (2 ml) was cooled to −78° C., and a solution of oxalyl chloride (62 μl, 0.71 mmol) in methylene chloride (2 ml) added dropwise. The mixture was allowed to warm slightly for 1 minute, then recooled to −78° C. To this mixture was added dropwise a solution of 4-[2-hydroxy-3-(2-methylbenzothiazol-5-yloxy)propyl]-piperazine-1-carboxylic acid tert-butyl ester (163.5 mg, 0.4 mmol) plus one drop of dimethylsulfoxide in the minimum amount of methylene chloride. The reaction mixture was allowed to warm slightly for 1 minute, then recooled to −78° C. To this mixture triethylamine (0.28 μl, 2.01 mmol) was added dropwise, and the mixture stirred at −78° C. for 15 minutes, then allowed to warm slowly to room temperature. Water (5 ml) was added, and the organic layer separated. The aqueous solution was extracted with methylene chloride, and the combined organics washed with brine, then dried over magnesium sulfate. The solvent was evaporated under reduced pressure to yield a liquid. This crude material, tert-butyl 4-[3-(2-methylbenzothiazol-5-yloxy)-2-oxopropyl]piperazinecarboxylate, a compound of formula (6), was used in the next reaction with no further purification.

B. Preparation of a Compound of Formula (6) in which R¹, R², R³, R⁵, R⁶, R⁷, and R⁸ are Hydrogen, R⁴ is (S)-Methyl, and R¹⁰ is 2-Methylbenzothiazol-5-yl

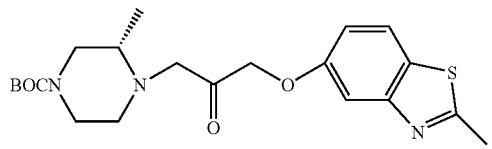

Similarly, following the procedure of Example 2A above, but replacing 4-[2-hydroxy-3-(2-methylbenzothiazol-5-yloxy)propyl]-piperazine-1-carboxylic acid tert-butyl ester with tert-butyl(3S)-4-[(2R)-2-hydroxy-3-(2-methylbenzothiazol-5-yloxy)propyl]-3-methylpiperazinecarboxylate, the following compound of formula (6) is prepared.

tert-butyl(3S)-3-methyl-4-[3-(2-methylbenzothiazol-5-yloxy)-2-oxopropyl]piperazinecarboxylate.

C. Preparation of a Compound of Formula (6), Varying R¹, R², R³, R⁴, R⁵, R⁶, R⁷, R⁸ and R¹⁰

Similarly, following the procedure of Example 2A or 2C above, but replacing 2-methyl-5-(oxiran-2-ylmethoxy)benzothiazole with other compounds of formula (5), other compounds of formula (6) are prepared.

EXAMPLE 3

A. Preparation of a Compound of Formula (7) in which R¹, R², R³, R⁴, R⁵, R⁶, R⁷, and R⁸ are Hydrogen, and R¹⁰ is 2-Methylbenzothiazol-5-yl

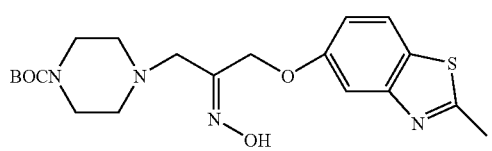

The crude product from Example 2A, tert-butyl 4-[3-(2-methylbenzothiazol-5-yloxy)-2-oxopropyl]piperazinecarboxylate, (1.236 g) was dissolved in a mixture of tetrahydrofuran (20 ml) and triethylamine (1.6 ml, 11.7 mmol). Hydroxylamine hydrochloride (446 mg, 6.46 mmol) was added to this solution, and the mixture was stirred overnight at room temperature. Solvent was removed under reduced pressure, and the residue partitioned between methylene chloride and water. The product, tert-butyl 4-[2-(hydroxyimino)-3-(2-methylbenzothiazol-5-yloxy)propyl]piperazinecarboxylate, was used in the next reaction without further purification.

B. Preparation of other Compounds of Formula (7)

Similarly, following the procedure of Example 3A above, but replacing tert-butyl 4-[3-(2-methylbenzothiazol-5-yloxy)-2-oxopropyl]piperazinecarboxylate with other compounds of formula (6), other compounds of formula (7) are prepared.

EXAMPLE 4

A. Preparation of a Compound of Formula (8) in which R¹, R², R³, R⁴, R⁵, R⁶, R⁷, and R⁸ are Hydrogen, and R¹⁰ is 2-Methylbenzothiazol-5-yl

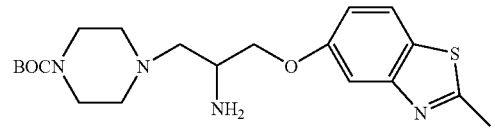

The crude product from Example 3A, tert-butyl 4-[2-(hydroxyimino)-3-(2-methylbenzothiazol-5-yloxy)propyl]piperazinecarboxylate (0.949 g) was suspended in a mixture of methanol (10 ml) and one drop of 40% aqueous hydrobromic acid. The suspension was mixed with Raney Nickel (one spatula) and shaken overnight in a Parr apparatus under hydrogen at about 50 psi. The mixture was then filtered, solvent removed from the filtrate under reduced pressure, and the residue partitioned between methylene chloride and water. Solvent was removed from the organic layer under reduced pressure, and the residue, tert-butyl 4-[2-amino-3-(2-methylbenzothiazol-5-yloxy)propyl]piperazinecarboxylate, used in the next reaction with no further purification.

B. Preparation of Other Compounds of Formula (8)

Similarly, following the procedure of Example 4A above, but replacing tert-butyl 4-[2-(hydroxyimino)-3-(2-methylbenzothiazol-5-yloxy)propyl]piperazinecarboxylate with other compounds of formula (7), other compounds of formula (8) are prepared.

EXAMPLE 5

A. Preparation of a Compound of Formula (9) in which R¹, R², R³, R⁴, R⁵, R⁶, R⁷, and R⁸ are Hydrogen, R¹⁰ is 2-Methylbenzothiazol-5-yl, and R is Acetyl

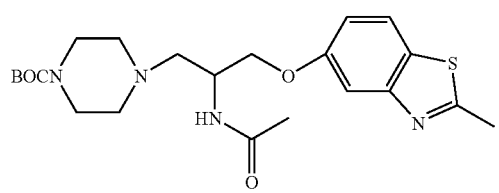

To a solution of tert-butyl 4-[2-amino-3-(2-methylbenzothiazol-5-yloxy)propyl]-piperazinecarboxylate (260 mg) and 4-dimethylaminopyridine (3 mg) in methylene chloride (6 ml) and triethylamine (178 µl) at 0° C. was added acetic anhydride (160 mg), and the mixture allowed to warm to room temperature. After stirring overnight, the mixture was partitioned between methylene chloride and water, and solvent removed from the organic layer under reduced pressure. The residue was chromatographed on a silica gel column, eluting with 25% ethyl acetate/hexanes followed by 10% methanol/methylene chloride, to provide crude tert-butyl 4-[2-(acetylamino)-3-(2-methylbenzothiazol-5-yloxy)propyl]piperazinecarboxylate, which was purified by preparative TLC.

B. Preparation of a Compound of Formula (9) in which $R^1$, $R^2$, $R^3$, $R^4$, $R^5$, $R^6$, $R^7$, and $R^8$ are Hydrogen, $R^{10}$ is 2-Methylbenzothiazol-5-yl, and R is —$SO_2CH_3$ Similarly, following the procedure of Example 5A above, but replacing acetic anhydride with methanesulfonylchloride, tert-butyl 4-{3-(2-methylbenzothiazol-5-yloxy)-2-[(methylsulfonyl)amino]propyl}piperazinecarboxylate was prepared.

C. Preparation of Other Compounds of Formula (9)

Similarly, following the procedure of Example 5A above, but replacing tert-butyl 4-[2-amino-3-(2-methylbenzothiazol-5-yloxy)propyl]-piperazinecarboxylate with other compounds of formula (8), other compounds of formula (9) are prepared.

EXAMPLE 6

A. Preparation of a Compound of Formula (10) in which $R^1$, $R^2$, $R^3$, $R^4$, $R^5$, $R^6$, $R^7$, and $R^8$ are Hydrogen, $R^{10}$ is 2-Methylbenzothiazol-5-yl, and R is Acetyl

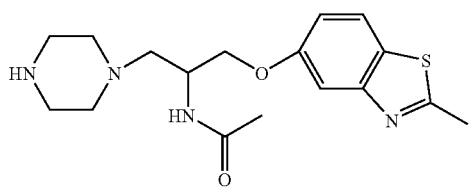

To a solution of tert-butyl 4-[2-(acetylamino)-3-(2-methylbenzothiazol-5-yloxy)propyl]piperazinecarboxylate (33.3 mg) in dioxane (1 ml) was added 4N hydrochloric acid in dioxane (1 ml) at room temperature, and the mixture stirred overnight. Solvent was removed from the mixture under reduced pressure, and the residue dried under vacuum, to provide N-[2-(2-methylbenzothiazol-5-yloxy)-1-(piperazinylmethyl)ethyl]acetamide as the dihydrochloride salt (34 mg).

B. Preparation of a Compound of Formula (10) in which $R^1$, $R^2$, $R^3$, $R^4$, $R^5$, $R^6$, $R^7$, and $R^8$ are Hydrogen, $R^{10}$ is 2-Methylbenzothiazol-5-yl, and R is —$SO_2CH_3$ Similarly, following the procedure of Example 6A above, but replacing tert-butyl 4-[2-(acetylamino)-3-(2-methylbenzothiazol-5-yloxy)propyl]piperazinecarboxylate with tert-butyl 4-{3-(2-methylbenzothiazol-5-yloxy)-2-[(methylsulfonyl)amino]propyl}piperazinecarboxylate, [2-(2-methylbenzothiazol-5-yloxy)-1-(piperazinylmethyl)ethyl](methylsulfonyl)amine was prepared.

C. Preparation of Other Compounds of Formula (10)

Similarly, following the procedure of Example 6A above, but replacing tert-butyl 4-[2-(acetylamino)-3-(2-methylbenzothiazol-5-yloxy)propyl]piperazinecarboxylate with other compounds of formula (9), other compounds of formula (10) are prepared.

EXAMPLE 7

A. Preparation of a Compound of Formula I in which $R^1$, $R^2$, $R^3$, $R^4$, $R^5$, $R^6$, $R^7$ and $R^8$ are Hydrogen, $R^{10}$ is 2-Methylbenzothiazol-5-yl, $R^9$ is —NHC(O)$CH_3$, X is 3-Phenylphenyl, n is 0 so that Y is a Covalent Bond, and Z is —NH—C(O)—$CH_2$—N<

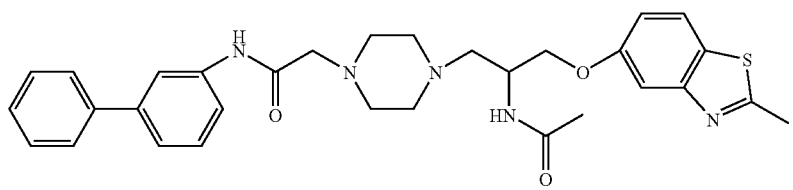

To a solution of N-[2-(2-methylbenzothiazol-5-yloxy)-1-(piperazinylmethyl)ethyl]-acetamide (18.4 mg) in N,N-dimethylformamide (2 ml) was added ethyldiisopropylamine (500 µl) and chloro-N-(3-phenylphenyl)amide (15.6 mg). The mixture was heated at 75° C. overnight, then solvent removed under reduced pressure, and the residue dissolved in a mixture of methanol/methylene chloride and applied to a preparative TLC plate. The plate was eluted with 4% methanol/methylene chloride and the appropriate fraction collected, providing 2-{4-[2-(acetylamino)-3-(2-methylbenzothiazol-5-yloxy)propyl]piperazinyl}-N-(3-phenylphenyl)acetamide (10 mg).
$^1$H NMR (CDCl$_3$, 400 MHz): δ 9.20 (brs, 1H); 7.79 (brs, 1H); 7.72 (d, 1H); 7.67-7.60 m, 3H); 7.51-7.37 (m, 6H); 7.04 (dd, 1H); 6.10 (brs, 1H); 4.52-4.41 (m, 1H); 4.24 (dd, 1H); 4.17 (dd, 1H); 3.19 (s, 2H); 2.85 (s, 3H); 2.85-2.60 (m, 10H); 2.08 (s, 3H).

B. Preparation of a Compound of Formula I in which $R^1$, $R^2$, $R^3$, $R^4$, $R^5$, $R^6$, $R^7$, and $R^8$ are Hydrogen, $R^{10}$ is 2-Methylbenzothiazol-5-yl, $R^9$ is —NHSO$_2$CH$_3$, X is 3-Phenylphenyl, Y is a Covalent Bond, and Z is —NH—C(O)—CH$_2$—N<

Similarly, following the procedure of Example 7A above, but replacing N-[2-(2-methylbenzothiazol-5-yloxy)-1-(piperazinylmethyl)ethyl]acetamide with [2-(2-methylbenzothiazol-5-yloxy)-1-(piperazinylmethyl)ethyl](methylsulfonyl)amine, 2-(4-{3-(2-methylbenzothiazol-5-yloxy)-2-[(methylsulfonyl)amino]propyl}piperazinyl)-N-(3-phenylphenyl)acetamide was prepared.

$^1$H NMR (CDCl$_3$, 400 MHz): δ 9.19 (brs, 1H); 7.79 (brs, 1H); 7.74 (d, 1H); 7.67-7.61 (m, 3H); 7.50-7.37 (m, 6H); 7.04 (dd, 1H); 5.20 (brs, 1H); 4.22-4.18 (m, 2H); 4.10-3.98 (m, 1H); 3.21 (brs, 2H); 3.12 (s, 3H); 2.86 (s, 3H); 2.80-2.60 (m, 10H).

C. Preparation of Other Compounds of Formula I

Similarly, following the procedure of Example 7A above, but replacing N-[2-(2-methylbenzothiazol-5-yloxy)-1-(piperazinylmethyl)ethyl]acetamide with other compounds of formula (10), other compounds of Formula I are prepared.

EXAMPLE 8

A. Preparation of a Compound of Formula I in which R$^1$, R$^2$, R$^3$, R$^4$, R$^5$, R$^6$, R$^7$ and R$^8$ are Hydrogen, R$^{10}$ is 2-Methylbenzothiazol-5-yl, R$^9$ is —NHC(O)CH$_3$, X is Fluoren-2-yl, n is 0 so that Y is a Covalent Bond, and Z is —NHC(O)N<

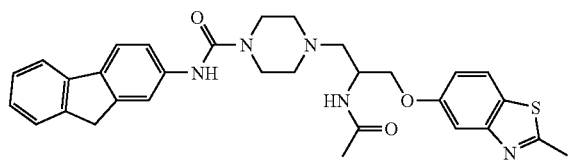

To a solution of N-[2-(2-methylbenzothiazol-5-yloxy)-1-(piperazinylmethyl)ethyl]-acetamide (18.4 mg) in tetrahydrofuran (1 ml) was added triethylamine (25.6 µl) and 2-fluorenyl isocyanate (9.5 mg). The reaction mixture was stirred at 55° C. for 4 hours, producing a white precipitate. The precipitate was filtered off, and solvent removed from the filtrate under reduced pressure. The residue was purified by thin layer chromatography, developing with 4% methanol/methylene chloride, to provide N-{2-[4-(N-fluoren-2-ylcarbamoyl)piperazinyl]-1-[(2-methylbenzothiazol-5-yloxy)methyl]ethyl}acetamide (11.2 mg), a compound of Formula I.

$^1$H NMR (CDCl$_3$, 400 MHz): δ 7.76-7.68 (m, 4H); 7.57 (d, 1H); 7.48 (brs, 1H); 7.38 (t, 1H); 7.30-7.21 (m, 2H); 7.03 (dd, 1H); 6.60 (brs, 1H); 6.03 (brs, 1H); 4.56-4.42 (m, 1H); 4.24 (dd, 1H); 4.17 (dd, 1H); 3.89 (s, 2H); 3.60-3.50 (m, 4H); 2.86 (s, 3H); 2.80-2.56 (m, 6H); 2.08 (s, 3H).

B. Preparation of a Compound of Formula I in which R$^1$, R$^2$, R$^3$, R$^4$, R$^5$, R$^6$, R$^7$ and R$^8$ are Hydrogen, R$^{10}$ is 2-Methylbenzothiazol-5-yl, R$^9$ is —NHSO$_2$CH$_3$, X is Fluoren-2-yl, n is 0 so that Y is a Covalent Bond, and Z is —NHC(O)N<

Similarly, following the procedure of Example 8A above, but replacing N-[2-(2-methylbenzothiazol-5-yloxy)-1-(piperazinylmethyl)ethyl]-acetamide with [2-(2-methylbenzothiazol-5-yloxy)-1-(piperazinylmethyl)ethyl](methylsulfonyl)amine, N-fluoren-2-yl(4-{3-(2-methylbenzothiazol-5-yloxy)-2-[(methylsulfonyl)amino]propyl}piperazinyl)-carboxamide was prepared.

$^1$H NMR (CDCl$_3$, 400 MHz): δ 7.78-7.65 (m, 4H); 7.58 (d, 1H); 7.47 (d, 1H); 7.30-7.23 (m, 2H); 7.01 (dd, 1H); 4.22-4.18 (m, 2H); 4.18-4.03 (m, 1H); 3.90 (brs, 2H); 3.78-3.60 (m, 4H); 3.12 (s, 3H); 2.86 (s, 3H); 2.90-2.65 (m, 6H).

C. Preparation of Other Compounds of Formula I

Similarly, following the procedure of Example 8A above, but replacing but replacing N-[2-(2-methylbenzothiazol-5-yloxy)-1-(piperazinylmethyl)ethyl]-acetamide with other compounds of formula (10), other compounds of Formula I are prepared.

EXAMPLE 9

A. Preparation of a Compound of Formula I in which R$^1$, R$^2$, R$^3$, R$^4$, R$^5$, R$^6$, R$^7$ and R$^8$ are Hydrogen, R$^{10}$ is 2-Methylbenzothiazol-5-yl, R$^9$ is —OCH$_3$, X is 4-(Trifluoromethyl)phenyl]-(1,2,4-oxadiazol-3-yl, Y is —CH$_2$—, and Z is —N<

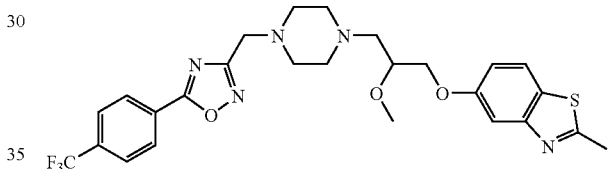

A solution of 3-(2-methylbenzothiazol-5-yloxy)-1-[4-({5-[4-(trifluoromethyl)phenyl]-(1,2,4-oxadiazol-3-yl)}methyl)piperazinyl]propan-2-ol (0.10 g) in toluene (6 ml) was added to a suspension of sodium hydride (0.09 g) in toluene (2 ml) at 0° C. The mixture was stirred at 100° C. for 2 hours, then cooled to 0° C. Methyl iodide (0.14 ml) was then added, and the mixture stirred overnight at room temperature. After slow addition of water the mixture was extracted with ethyl acetate, washed with brine, dried over magnesium sulfate, and the solvent removed under reduced pressure. The residue was purified by flash chromatography (3% methanol in methylene chloride), to provide 5-{2-methoxy-3-[4-({5-[4-(trifluoromethyl)phenyl](1,2,4-oxadiazol-3-yl)}methyl)piperazinyl]propoxy}-2-methylbenzothiazole (0.0075 g).

$^1$H NMR (400 MHz, CDCl$_3$, δ): 8.28 (d, 2H); 7.79 (d, 2H); 7.65 (d, 1H); 7.63 (s, 1H); 7.00 (d, 1H); 4.15-4.19 (m, 1H); 4.04-4.08 (d, 2H); 3.79 (m, 2H); 3.50 (s, 3H); 3.48 (s, 2H); 2.80 (s, 3H); 2.54-2.74 (m, 8H).

B. Preparation of Other Compounds of Formula I

Similarly, following the procedure of Example 9A above, but replacing but replacing 3-(2-methylbenzothiazol-5-yloxy)-1-[4-({5-[4-(trifluoromethyl)phenyl]-(1,2,4-oxadiazol-3-yl)}methyl)piperazinyl]propan-2-ol with other compounds of formula (11), other compounds of Formula I are prepared where R$^9$ is —OR$^{12}$.

EXAMPLE 10

Preparation of a Compound of Formula (3)

Preparation of a Compound of Formula (3) in which $R^{10}$ is 2-Methylbenzothiazol-5-yl

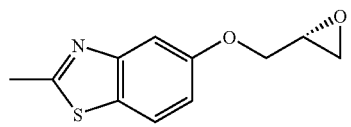

A mixture of 2-methylbenzothiazol-5-ol (6.0 g, 36 mmol), (S)-(+)-epichlorohydrin (20 ml, 182 mmol), and potassium carbonate (20 g, 144 mmol) in acetone (100 ml), was heated to reflux and allowed to stir overnight. The solution was allowed to cool and filtered through Celite 512. The filtrate was evaporated under reduced pressure to yield an oil, which was chromatographed on silica gel, eluting with 20% ethyl acetate/hexanes, to yield 2-methyl-5-(R)-(oxiran-2-yl-methoxy)benzothiazole as white solid.

EXAMPLE 11

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 12

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 13

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 14

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 15

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 16

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water.

The sodium benzoate, flavor, and color are diluted with some of the water and added with stirring. Sufficient water is then added to produce the required volume.

EXAMPLE 17

A subcutaneous formulation may be prepared as follows:

| Ingredient | Quantity |
|---|---|
| Active Ingredient | 5.0 mg |
| Corn Oil | 1.0 mL |

EXAMPLE 18

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 19

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 20

Sustained Release Composition

| Ingredient | Weight Range (%) | Preferred Range (%) | Most Preferred |
|---|---|---|---|
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 21

Mitochondrial Assays

Rat heart mitochondria are isolated by the method of Nedergard and Cannon (Methods in Enzymol. 55, 3, 1979).

Palmitoyl CoA oxidation—The Palmityl CoA oxidation is carried out in a total volume of 100 micro liters containing the following agents: 110 mM KCl, 33 mM Tris buffer at pH 8, 2 mM KPi, 2 mM $MgCl_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention are added in a DMSO solution at the following concentrations: 100 micro molar, 30 micro molar, and 3 micro molar. In each assay, a DMSO control is used. After 15 min at 30° C., the enzymatic reaction is centrifuged (20,000 g for 1 min), and 70 microliters of the supernatant is added to an activated reverse phase silicic acid column (approximately 0.5 ml of silicic acid). The column is eluted with 2 ml of water, and 0.5 ml of the eluent is used for scintillation counting to determine the amount of $C^{14}$ trapped as $C^{14}$ bicarbonate ion.

The compounds of the invention show activity as fatty acid oxidation inhibitors in this assay.

2-{4-[2-(acetylamino)-3-(2-methylbenzothiazol-5-yloxy)propyl]piperazinyl}-N-(3-phenylphenyl)acetamide; Palm CoA inhibition $IC_{50}$ 12.7 µM.

N-{2-[4-(N-fluoren-2-ylcarbamoyl)piperazinyl]-1-[(2-methylbenzothiazol-5-yloxy)methyl]ethyl}acetamide; Palm CoA inhibition $IC_{50}$ 8.2 µM.

2-(4-{3-(2-methylbenzothiazol-5-yloxy)-2-[(methylsulfonyl)amino]propyl}piperazinyl)-N-(3-phenylphenyl)acetamide; Palm CoA inhibition $IC_{50}$ 2.9 µM.

N-fluoren-2-yl(4-{3-(2-methylbenzothiazol-5-yloxy)-2-[(methylsulfonyl)amino]propyl}-piperazinyl)carboxamide; Palm CoA inhibition $IC_{50}$ 3.0 µM.

EXAMPLE 22

Perfusate

Langendorff perfusion is conducted using a Krebs-Henseleit solution containing: (mM) NaCl (118.0), KCl (4.7), $KH_2PO_4$ (1.2), $MgSO_4$ (1.2), $CaCl_2$ (2.5), $NaHCO_3$ (25.0) and glucose (5.5 or 11) (Finegan et al. 1996). The working heart perfusate consists of a Krebs-Henseleit solution with the addition of palmitate (0.4 or 1.2 mM) pre-bound to 3% bovine serum albumin (essentially fatty acid free BSA) and insulin (100 µU/ml). Palmitate is initially dissolved in an ethanol:water mixture (40%:60%) containing 0.5-0.6 g $Na_2CO_3$ per g of palmitate. Following heating to evaporate the ethanol, this mixture is then added to the 3% BSA-Krebs-Henseleit mixture (without glucose) and allowed to dialyze (8000 MW cut-off) overnight in 10 volumes of glucose-free Krebs-Henseleit solution. The next day, glucose is added to the solution and the mixture is filtered through glass microfiber filters (GF/C, Whatman, Maidstone, England) and kept on ice, or refrigerated, prior to use. The perfusate is continuously oxygenated with a 95% $CO_2$, 5% $O_2$ gas mixture while in the perfusion apparatus to main aerobic conditions.

Heart Perfusion Protocols

Rats are anesthetized with pentobarbital (60 mg/kg, intraperitoneally) and hearts are rapidly removed and placed in ice-cold Krebs-Henseleit solution. The hearts are then rapidly cannulated via the aortic stump and Langendorff perfusion at constant pressure (60 mm Hg) is initiated and continued for a 10-min equilibration period. During this equilibration period, the pulmonary artery is cut, and excess fat and lung tissue removed to reveal the pulmonary vein. The left atrium is cannulated and connected to the preload line originating from the oxygenation chamber. After the 10-min equilibration period, hearts are switched to working mode (by clamping off the Langendorff line and opening the preload and afterload lines) and perfused at 37° C. under aerobic conditions at a constant left atrial preload (11.5 mm Hg) and aortic afterload (80 mm Hg). The compliance chamber is filled with air adequate to maintain developed pressure at 50-60 mm Hg. Perfusate is delivered to the oxygenation chamber via a peristaltic pump from the reservoir chamber that collected aortic and coronary flows as well as overflow from the oxygenator.

Typically, hearts are perfused under aerobic conditions for 60 minutes. Hearts are paced at 300 beats/min throughout each phase of the perfusion protocol (voltage adjusted as necessary) with the exception of the initial 5 min of reperfusion when hearts are allowed to beat spontaneously.

At the end of the perfusion protocol, hearts are rapidly frozen using Wollenberger clamps cooled to the temperature of liquid nitrogen. Frozen tissues are pulverized and the resulting powders stored at −80° C.

Myocardial Mechanical Function

Aortic systolic and diastolic pressures are measured using a Sensonor (Horten Norway) pressure transducer attached to the aortic outflow line and connected to an AD Instruments data acquisition system. Cardiac output, aortic flow and coronary flow (cardiac output minus aortic flow) are measured (ml/min) using in-line ultrasonic flow probes connected to a Transonic T206 ultrasonic flow meter. Left ventricular minute work (LV work), calculated as cardiac output x left ventricular developed pressure (aortic systolic pressure-preload pressure), is used as a continuous index of mechanical function. Hearts are excluded if LV work decreased more than 20% during the 60-min period of aerobic perfusion.

Myocardial Oxygen Consumption and Cardiac Efficiency

Measuring the atrial-venous difference in oxygen content of the perfusate and multiplying by the cardiac output provides an index of oxygen consumption. Atrial oxygen content (mmHg) is measured in perfusate in the preload line or just prior to entering the left atria. Venous oxygen content is measured from perfusate exiting the pulmonary artery and passing through in-line $O_2$ probes and meters Microelectrodes Inc., Bedford, N.H. Cardiac efficiency is calculated as the cardiac work per oxygen consumption.

Measurement of Glucose and Fatty Acid Metabolism

Determining the rate of production of $^3H_2O$ and $^{14}CO_2$ from $[^3H/^{14}C]$glucose isolated working rat model allows a direct and continuous measure of the rates of glycolysis and glucose oxidation. Alternatively, the measure of the production of $^3H_2O$ from [5-$^3H$]palmitate provides a direct and continuous measure of the rate of palmitate oxidation. Dual labelled substrates allows for the simultaneous measure of either glycolysis and glucose oxidation or fatty acid oxidation and glucose oxidation. A 3-ml sample of perfusate is taken from the injection port of the recirculating perfusion apparatus at various time-points throughout the protocol for analysis of $^3H_2O$ and $^{14}CO_2$ and immediately placed under mineral oil until assayed for metabolic product accumulation. Perfusate is supplemented with $[^3H/^{14}C]$glucose or [5-$^3H$]palmitate to approximate a specific activity of 20 dpm/mmol. Average rates of glycolysis and glucose oxidation are calculated from linear cumulative time-courses of product accumulation between 15 and 60 minutes for aerobic perfusion. Rates of glycolysis and glucose oxidation are expressed as µmol glucose metabolized/min/g dry wt.

Measurement of Myocardial Glycolysis

Rates of glycolysis are measured directly as previously described (Saddik & Lopaschuk, 1991) from the quantitative determination of $^3H_2O$ liberated from radiolabeled [5-$^3H$] glucose at the enolase step of glycolysis. Perfusate samples are collected at various time-points throughout the perfusion protocol. $^3H_2O$ is separated from the perfusate by passing perfusate samples through columns containing Dowex 1-X 4 anion exchange resin (200-400 mesh). A 90 g/L Dowex in 0.4 M potassium tetraborate mixture is stirred overnight, after which 2 ml of the suspension is loaded into separation columns and washed extensively with $dH_2O$ to remove the tetraborate. The columns are found to exclude 98-99.6% of the total [$^3H$]glucose (Saddik & Lopaschuk, 1996). Perfusate samples (100 µl) are loaded onto the columns and washed with 1.0 ml $dH_2O$. Effluent is collected into 5 ml of Ecolite Scintillation Fluid (ICN, Radiochemicals, Irvine, Calif.) and counted for 5 min in a Beckman LS 6500 Scintillation Counter with an automatic dual ($^3H/^{14}C$) quench correction program. Average rates of glycolysis for each phase of perfusion are expressed as μmol glucose metabolized/min/g dry wt as described above.

Measurement of Myocardial Glucose Oxidation

Glucose oxidation is also determined directly as previously described (Saddik & Lopaschuk, 1991) by measuring $^{14}CO_2$ from [$^{14}C$]glucose liberated at the level of pyruvate dehydrogenase and in the Krebs cycle. Both $^{14}CO_2$ gas exiting the oxygenation chamber and [$^{14}C$]bicarbonate retained in solution are measured. Perfusate samples are collected at various time-points throughout the perfusion protocol. $^{14}CO_2$ gas is collected by passing the gas exiting the oxygenator through a hyamine hydroxide trap (20-50 ml depending on perfusion duration). Perfusate samples (2×1 ml), which were stored under oil to prevent the escape of gas by equilibration with atmospheric $CO_2$, are injected into 16×150 mm test tubes containing 1 ml of 9 N $H_2SO_4$. This process releases $^{14}CO_2$ from the perfusate present as $H^{14}CO_3$—. These duplicate tubes are sealed with a rubber stopper attached to a 7-ml scintillation vial containing a 2×5 cm piece of filter paper saturated with 250 μl of hyamine hydroxide. The scintillation vials with filter papers are then removed and Ecolite Scintillation Fluid (7 ml) added. Samples are counted by standard procedures as described above. Average rates of glucose oxidation for each phase of perfusion are expressed as μmol glucose metabolized/min/g dry wt as described above.

Measurement of Myocardial Fatty Acid Oxidation

Rates of palmitate oxidation are measured directly as previously described (Saddik & Lopaschuk, 1991) from the quantitative determination of $^3H_2O$ liberated from radiolabeled [5-$^3H$]palmitate. $^3H_2O$ is separated from [5-$^3H$]palmitate following a chloroform:methanol (1.88 ml of 1:2 v/v) extraction of a 0.5 ml sample of buffer then adding 0.625 ml of chloroform and 0.625 ml of a 2M KCL:HCl solution. The aqueous phase is removed and treated with a mixture of chloroform, methanol and KCl:HCl (1:1:0.9 v/v). Duplicate samples are taken from the aqueous phase for liquid scintillation counting and rates of oxidation are determined taking into account a dilution factor. This results in >99% extraction and separation of $^3H_2O$ from [5-$^3H$]palmitate. Average rates of glucose oxidation for each phase of perfusion are expressed as μmol glucose metabolized/min/g dry wt as described above.

Dry to Wet Ratios

Frozen ventricles are pulverized at the temperature of liquid nitrogen with a mortar and pestle. Dry to wet determinations are made by weighing a small amount of frozen heart tissue and re-weighing that same tissue after 24-48 hr of air drying and taking the ratio of the two weights. From this ratio, total dry tissue can be calculated. This ratio is used to normalize, on a per g dry weight basis, rates of glycolysis, glucose oxidation and glycogen turnover as well as metabolite contents.

The compounds of the invention showed activity as fatty acid oxidation inhibitors in the above assays.

REFERENCES

Finegan B A, Gandhi M, Lopaschuk G D, Clanachan A S, 1996. Antecedent ischemia reverses effects of adenosine on glycolysis and mechanical function of working hearts. *American Journal of Physiology* 271: H2116-25.

Saddik M, Lopaschuk G. D., 1991. Myocardial triglyceride turnover and contribution to energy substrate utilization in isolated working rat hearts. *Journal of Biological Chemistry* 266: 8162-8170.

All patens and publications cited above are hereby incorporated by reference.

We claim:
1. A compound of Formula I:

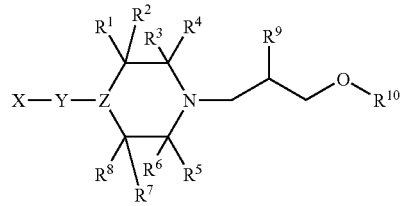

Formula I wherein:
$R^1$, $R^2$, $R^3$, $R^4$, $R^5$, $R^6$, $R^7$, and $R^8$ are hydrogen, lower alkyl, or —C(O)R; in which R is $NR^{12}R^{13}$, where $R^{12}$ and $R^{13}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl;

with the proviso that the maximum number of carbonyl groups is 2;

$R^9$ is —$NHSO_2R^{12}$, —$NHC(O)R^{12}$, or —$OR^{12}$;
in which $R^{12}$ is lower alkyl optionally substituted with halo, hydroxyl, or $CF_3$; and $R^{10}$ is 2-methylbenzo-1,3-thiazol-5-yl, 2-cyclohexylbenzo-1,3-thiazol-5-yl, 2-phenylbenzo-1,3-thiazol-5-yl, or 2-phenylbenz-1,3-oxazol-5-yl;

X is 5-[4-(trifluoromethyl)phenyl](1,2,4-oxadiazol-3-yl, 4,5-dihydroisoxazolyl, 1,3-oxazolinyl, 2,3-dihydro-1,2,4-oxadiazolyl, 4,5-dihydro-1,2,4-oxadiazolyl, 1,4-pyrazolinyl, or 4,5-dihydropyridinyl;

Y is $(CH_2)_n$, in which n is 0, 1, or 2; and

Z is —N<, —NH—C(O)—N<, or —NH—C(O)—$CH_2$—N<;

or a pharmaceutically acceptable salt thereof.

2. The compound of claim 1, wherein $R^1$, $R^2$, $R^3$, $R^4$, $R^5$, $R^6$, $R^7$, and $R^8$ are hydrogen or lower alkyl.

3. The compound of claim 2, wherein $R^{10}$ is 2-cyclohexylbenzo-1,3-thiazol-5-yl, 2-phenylbenzo-1,3-thiazol-5-yl, or 2-phenylbenz-1,3-oxazol-5-yl.

4. The compound of claim 2, wherein $R^9$ is —$OR^{12}$.

5. The compound of claim 4, wherein Z is —N<.

6. The compound of claim 2, wherein $R^9$ is —$NHC(O)R^{12}$.

7. The compound of claim 6, wherein Z is —NH—C(O)—N<.

8. The compound of claim 6, wherein Z is —NH—C(O)—$CH_2$—N<.

9. The compound of claim 2, wherein $R^9$ is —$NHSO_2R^{12}$.

10. The compound of claim 9, wherein Z is —NH—C(O)—N<.

11. The compound of claim 9, wherein Z is —NH—C(O)—$CH_2$—N<.

12. The compound of claim 1, wherein $R^1$, $R^2$, $R^3$, $R^4$, $R^5$, $R^6$, $R^7$, and $R^8$ are hydrogen, $R^{10}$ is 2-methylbenzo-1,3-thiazol-5-yl, $R^{12}$ is —$CH_3$, X is 5-[4-(trifluoromethyl)phenyl](1,2,4-oxadiazol-3-yl), and n is 1 so that Y is —$CH_2$—, namely, 5-{(2R)-2-methoxy-3-[4-({5-[4-(trifluoromethyl)phenyl](1,2,4-oxadiazol-3-yl)}methyl)piperazinyl]propoxy}-2-methylbenzothiazole.

13. The compound of claim 11, wherein $R^1$, $R^2$, $R^3$, $R^4$, $R^5$, $R^6$, $R^7$, and $R^8$ are hydrogen, and $R^{10}$ is 2-methylbenzo-1,3-thiazol-5-yl.

14. A method of treating a disease state chosen from diabetes, damage to skeletal muscles resulting from trauma or shock and a cardiovascular disease selected from atrial arrhythmia, intermittent claudication, ventricular arrhythmia, Prinzmetal's (variant) angina, stable angina, unstable angina, congestive heart disease, or myocardial infarction in a mammal by administration of a therapeutically effective dose of a compound of claim 1.

15. The method of claim 14, wherein the disease state is a cardiovascular disease selected from atrial arrhythmia, intermittent claudication, ventricular arrhythmia, Prinzmetal's (variant) angina, stable angina, unstable angina, congestive heart disease, or myocardial infarction.

16. The method of claim 14, wherein the disease state is diabetes.

17. A pharmaceutical composition comprising at least one pharmaceutically acceptable excipient and a therapeutically effective amount of a compound of claim 1.

* * * * *